United States Patent [19]

Suzuki et al.

[11] 4,288,544
[45] Sep. 8, 1981

[54] METHOD AND APPARATUS FOR MEASURING MICROORGANISM ACTIVITY

[75] Inventors: Shuichi Suzuki, Tokyo; Isao Karube, Tachikawa, both of Japan

[73] Assignee: Kyowa Hakko Kogyo Co., Ltd., Tokyo, Japan

[21] Appl. No.: 35,092

[22] Filed: May 1, 1979

[30] Foreign Application Priority Data

Aug. 23, 1978 [JP] Japan .................. 53-101897

[51] Int. Cl.$^3$ .................. C12Q 1/06; C12M 1/34
[52] U.S. Cl. ..................... 435/39; 204/1 T; 204/195 B; 204/195 R; 435/32; 435/291
[58] Field of Search .................. 435/4, 29, 32, 34, 36, 435/37, 38, 39, 40, 291, 287, 289, 817; 204/1 E, 1 T, 195 R, 195 B

[56] References Cited

U.S. PATENT DOCUMENTS

| | | | |
|---|---|---|---|
| 3,403,081 | 9/1968 | Rohrback et al. | 435/29 X |
| 3,506,544 | 4/1970 | Silverman et al. | 435/39 X |
| 3,539,455 | 11/1970 | Clark, Jr. | 204/1 E |
| 3,707,455 | 12/1972 | Derr et al. | 204/1 E X |
| 3,743,581 | 7/1973 | Cady et al. | 435/34 |
| 3,838,034 | 9/1974 | Groner | 435/817 X |
| 4,009,078 | 2/1977 | Wilkins et al. | 435/34 |
| 4,024,042 | 5/1977 | Enfors et al. | 435/817 X |
| 4,149,938 | 4/1979 | Young et al. | 435/291 |

FOREIGN PATENT DOCUMENTS 1433887 of 1973 United Kingdom .
1446182 of 1973 United Kingdom .
1529715 of 1975 United Kingdom .

OTHER PUBLICATIONS

Matsunaga et al., Analitica Chimica Acts, vol. 98, p. 25-30, 1978.

*Primary Examiner*—Robert J. Warden
*Attorney, Agent, or Firm*—Fitzpatrick, Cella, Harper & Scinto

[57] ABSTRACT

The microbial activity in a liquid medium is determined by measuring the electric current values or potential values generated by the microorganisms. Also disclosed herein is apparatus for carrying out such measurement comprising two electrodes or two electrolytic electrode systems constructed and arranged to be immersed in a culture liquor.

4 Claims, 2 Drawing Figures

METHOD AND APPARATUS FOR MEASURING MICROORGANISM ACTIVITY

BACKGROUND OF THE INVENTION

The present invention pertains to a method and apparatus for reliably, simply, rapidly and continuously measuring microbial activity in a microorganism-containing liquid.

The microorganism-containing liquid used in the present invention (hereinafter referred to as a culture liquor) means a culture liquor containing microorganisms or a microorganism suspension, prepared by separating living microorganism cells from a culture liquor and suspending the cells in another medium.

More particularly, the present invention relates to a method and apparatus for measuring microorganism activity, wherein the electrical properties originating from microorganism itself are measured by an electrochemical device.

Recently, fermentation processes are more widely being employed for the production of raw materials for food, medicine and the like. When such various useful compounds are produced by fermentation, it is very important in the effective and continuous performance of the fermentation process to measure the number or activity of microorganism cells in the culture liquor in each production step.

Heretofore, the conventional methods for measuring the number or activity of microorganisms in a fermentation batch were:

(1) Colony count method wherein the number of microorganism cells is determined by diluting the culture liquor, spraying the liquor on an agar plate medium and visually counting the number of colonies formed after a suitable incubation period. According to this method, it is possible to measure the number of microorganism cells, above all, the number of living cells.

(2) Optically measuring the turbidity of culture liquor caused by a Tyndall phenomenon and estimating the number of microorganism cells from degree of turbidity. According to this method, the number of the existing microorganism cells can be measured.

(3) Measuring the amount of adenosine triphosphate (ATP) enzymatically and estimating the number of microorganism cells therefrom. ATP, a high energy compound produced by microorganism cells in the culture liquor, can be regarded as being dependent upon the number of microorganisms and thus can be used as an index. According to this method, the number of living microorganism cells can be measured.

(4) Measuring the charged metabolites in the fermentation medium by determination of electric impedance. According to this method, the number of living microorganism cells can be obtained.

However, the foregoing known methods suffer from various disadvantages. For example, the colony count method is rather complicated in performance and operation, and it takes 24-48 hours of incubation before a count can be made. Moreover, the value obtained is not always reliable.

The method of measuring turbidity is based on an optical measurement, and a sample must be optically clear and isotropic. However, in industrial practices, media containing solid matters and colored media are more frequently used. Thus, it is actually very difficult to optically make an exact measurement of the number of cells.

According to the method wherein ATP is measured, luciferase is caused to react with ATP, and the fluorescent material thus formed are measured to obtain an amount of the corresponding ATP. As ATP or fluorescent materials exist in the medium it is difficult to exactly measure the amount of ATP originating from the microorganisms. As a result a reliable count of the number of microorganisms is not possible.

The method based on electric impedance suffers from the disadvantage that the measurement cannot be made under some aerobic conditions. Moreover, when a sample solution contains an electroconductive material, no measurement can be made. Since industrial fermentation processes are usually carried out under aerobic conditions, this method has no practical use.

In the cultivation of Actinomycetes and the like, many spores branch from individual cells with time, and many active parts appear. Similarly, the viscosity of the solution increases considerably with time, that is, with increasing number of cells and increasing branched spores. In the cultivation of such Actinomycetes, it is very important in the cultivation control to ascertain the number (activity) of the active parts rather than the number of cells, and no useful means for measuring the active parts was heretofore known.

As described above, the number or activity values of microorganisms so far measured according to any of the known methods has disadvantages, and it is the object of the present invention to realize a reliable and simple method for measuring microorganism activity in an industrial fermentation process.

SUMMARY OF THE INVENTION

It has been found that, when two electrodes (an exposed surface of one electrode being covered with a microorganism-impermeable membrane) are inserted into a culture liquor the difference between electric current values or potential values measured by the two electrodes corresponded very well to the microorganism activity.

It has also been found that when the two electrolytic electrode systems wherein each electrode system is constructed from two platinum electrodes and a saturated calomel electrode, and the platinum electrode (anode) of one electrode system is covered with a microorganism-impermeable membrane are inserted into a culture liquor and the potentials between the two electrodes of each system are controlled by a potentiostat, a difference between the electric current measured by the two electrolytic electrode systems corresponds very well to the microorganism activity.

Based upon the foregoing fundamental findings, the present invention provides a method for measuring microorganism activity, characterized by contacting electrode systems or electrolytic electrode systems with a culture liquor and measuring the electric current or potential generated by reaction of microorganisms (cells) with the these electrodes. One typical apparatus for measuring microorganism activity comprises two electrode systems, each having a cathode and an electrolyte inside, having a liquid junction for contact with an outside liquid and an exposed anode. In one of the electrode systems, the exposed anode is covered with a microorganism-impermeable membrane. A second embodiment of apparatus for measuring microorganism activity comprises two electrolytic electrode systems, each having two electrodes and a calomel electrode to keep a constant potential. One electrode (anode) of one electrolytic electrode system is covered with a microorganism-impermeable membrane.

For use in the present invention, any electrode of platinum, silver, gold, iron, etc. can be used for the cathode, and any insoluble electrode of platinum, silver, gold, etc. can be used for the anode.

The microorganisms whose activity can be measured according to the present invention include aerobic and anaerobic microorganisms such as bacteria, molds, yeasts, fungi, Actinomycetes, etc., and include all the microorganisms permitting measurement of an electric current or potential originating from the microorganism itself by the electrode systems or electrolytic electrode systems used.

In the cases of bacteria, yeasts, etc., the microorganism activity measured according to the present invention corresponds very well to the number of living cells in the culture liquor, and in such cases wherein there are active parts branching from individual cells such as Actinomycetes, it corresponds not to the number of living cells, but more importantly to total number of active parts of the microorganisms or dry weight of the cells.

The current values or voltage values measured according to the present invention depend upon temperature, pH, etc., and thus can be adjusted, if required. Being different from the optical method for measuring turbidity and the like, the present invention obviously has advantages such as not being influenced by liquid color, turbidity, etc.

The recognition of the correlation of the amount of microorganism cells to current values or potential values originating from the electrodes contacted with the microorganisms, are disclosed in Analytica Chimica Acta. 98 (1978), 25–30, authored by the inventors hereof, which description is expressly incorporated herein by reference.

BRIEF DESCRIPTION OF THE DRAWINGS

Certain specific embodiments of the invention have been chosen for purposes of illustration and description, and are shown in the accompanying drawings, forming a part of the specification wherein.

DETAILED DESCRIPTION OF THE INVENTION

Figure 1:
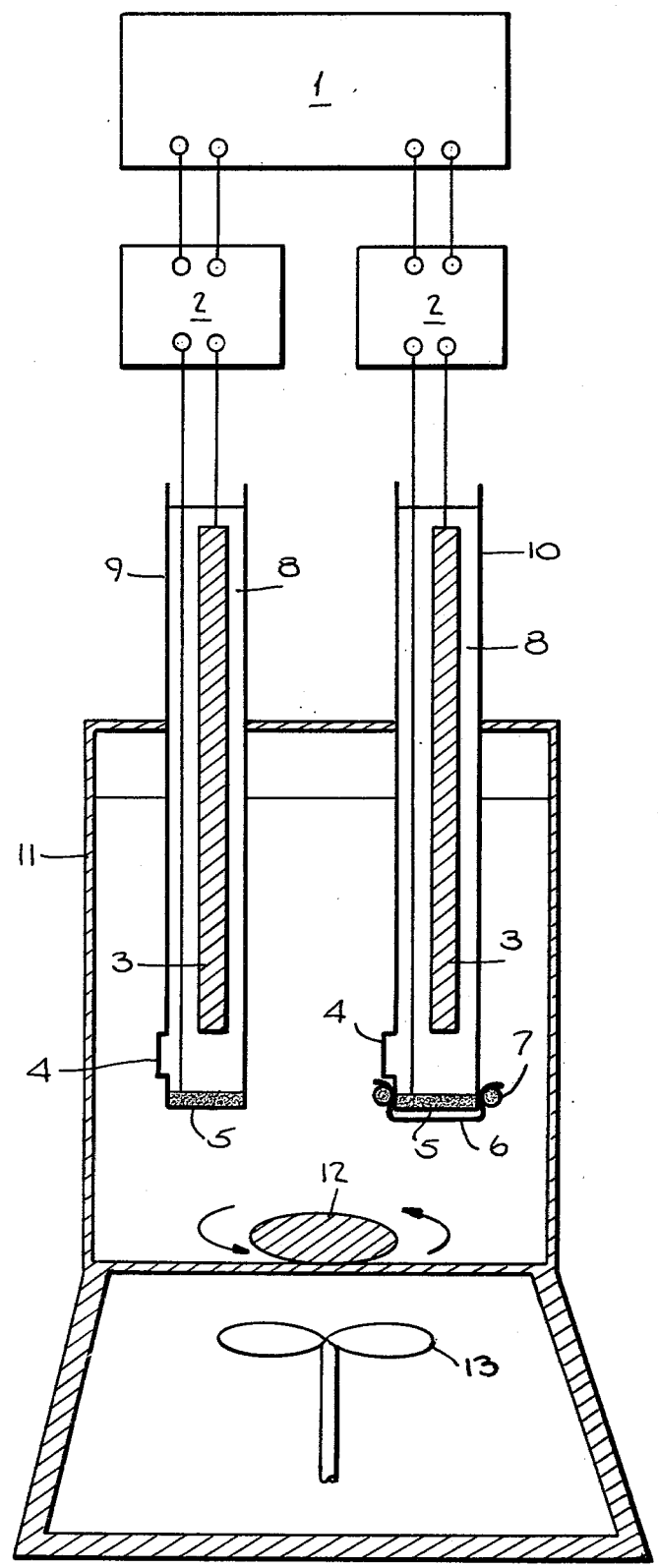
FIG. 1 is a diagrammatic illustration of one embodiment of an apparatus according to the invention.

With reference to FIG. 1, electrode systems designated by the numerals 9 and 10 are shown for insertion into a fermentation tank 11 having a stirring bar 12 and magnetic stirrer 13. Each electrode comprises a cathode 3, an electrolyte 8 inside and an anode 5. A liquid junction 4 is provided for contact with the outside liquid. In electrode 10 the anode 5 is platinum and is exposed while being covered with a microorganism-impermeable membrane 6. This electrode measures electroactive materials other than the microorganism cells existing in the fermentation liquor. The liquid junction of the electrodes 9 and 10, is preferably covered by a membrane (not shown) and for such purpose any membrane of low electric resistance, such as an ion exchange resin, ceramic, etc. can be used. For cathodes 3, metallic oxides, such as silver peroxide, silver chloride, silver dioxide, and the like or carbon or the like can be used. As the microorganism-impermeable membrane for covering the surface of exposed platinum anode 5 of electrode 10, any film such as a cellulose film or a millipore film can be used, so long as it can prevent the permeation of microorganism cells.

Connected to electrode 9 and electrode 10 respectively are an ammeter or potentiometer 2, and a recorder 1.

Those skilled in the art will appreciate that the apparatus schematically illustrated in FIG. 1 can be simplified or remodelled, if required, and can easily be microbiologically sterilized.

Figure 2:
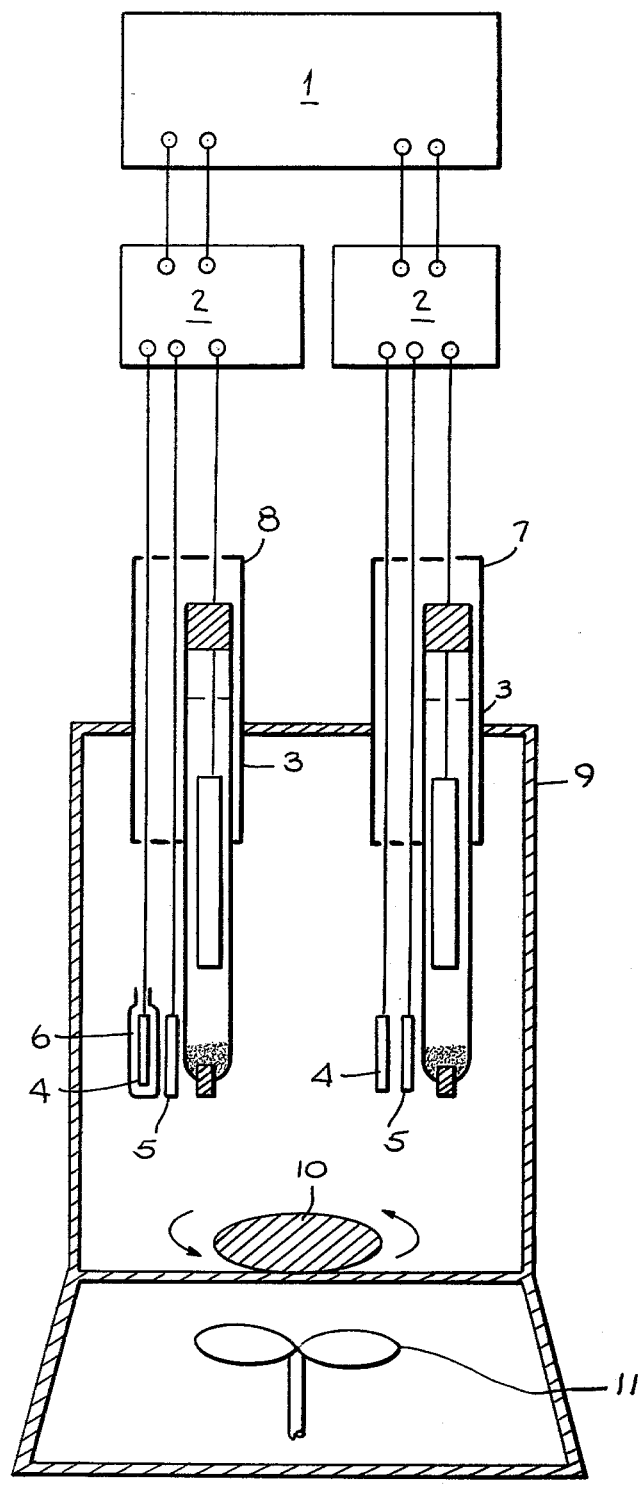
FIG. 2 is a diagrammatic illustration of a second embodiment of an apparatus according to the invention.

In FIG. 2 an alternative apparatus according to the invention in which two electrolytic electrode systems are used is schematically shown. Specifically, individual electrolytic electrode systems generally indicated by the numerals 7 and 8 each have one calomel electrode 3 and two electrode plates 4, 5. The systems are adapted to be set in a fermentation liquor in a fermentation tank 9 having a stirring bar 10 and magnetic stirrer 11. The exposed anode 4 of system 8 is covered with a microorganism-impermeable membrane 6 to measure electroactive materials other than the microorganism cells. As the microorganism-impermeable membrane, any membrane such as a cellulose film or a millipore film, or the like can be used, so long as it can prevent permeation of the microorganism cells. The electrode parts of the two electrolytic electrode systems are each connected to a potentiostat 2 and to a recorder 1.

As in the embodiment of FIG. 1, the apparatus schematically illustrated in FIG. 2 can be simplified and remodelled, if required, and of course can be microbiologically sterilized.

The microorganism activity in a cultivation tank is measured by an apparatus of the invention in the following manner. The microorganisms (living cells) and electrode active materials in the fermentation liquor (for example, formic acid, hydrogen, coenzyme, etc.) generate an electric current or a potential through contact with the anode of one of the electrode systems. On the other hand, only the electrode active materials contact with the anode of other electrode systems to generate an electric current or a potential. When the culture liquor is centrifuged to remove the cells, and when an electric current or potential of the supernatant liquor is measured, the current value or potential value of the two electrode systems are substantially identical with each other. Furthermore, when the culture liquor is sterilized by steaming, etc., and then subjected to measurement, the current values or potential values of the electrode systems are substantially identical with each other (the current value or value itself is lowered in both cases than when the living microorganisms exist).

The difference in the current values or potential values measured by the two electrode systems corresponded very well to the microorganism activity (number of cells, etc.) as confirmed by measurement by a known method. Thus, the difference in the current values or potential values of the electrode systems is regarded as an electric signal in correlation to the microorganism activity; and such activity determined reliably on such values.

The same mechanism is confirmed in the case of the electrolytic electrode system.

The exact mechanism of the phenomena and the principle has not been clarified. Yet, it is possible to measure the microorganism activity by measuring the electric properties originating from the electrodes contacted with the microorganism itself.

The following will further illustrate the invention.

EXAMPLE 1

In this example, bread yeast (*Saccharomyces cerevisiae* ATCC 7754) is inoculated into 1 L of a medium (pH 7.0) containing 40 g of glucose, 10 g of peptone, 5 g of yeast extract, 5 g of $KH_2PO_4$ and 2 g of $MgSO_4$, placed in a small cultivating jar fermenter (Model MD-26 made by Marubishi Rika Co., Ltd.) and subjected to aerobic cultivation at 37° C.

A disk platinum electrode having a diameter of 1 cm as the anode, a silver peroxide electrode (1 cm×4 cm) as the cathode, Selemion, a kind of anion exchange membrane as a liquid junction (type AMV made by Asahi Glass Co., Ltd.), and 0.1 M phosphate buffer solution (pH 7.0) as an electrolyte are used as the electrode systems. Two of such electrode systems in which the anode surface of one of the electrode systems is covered with a cellulose membrane for dialysis are inserted in the fermenter to conduct measurement. The relationship between the differences ($\Delta I$) in current values between the two electrode systems and number of cells at various time periods as determined separately by the colony count method are shown in Table 1.

TABLE 1

| Time (hr) | 3 | 5 | 8 | 10 | 12 | 15 |
|---|---|---|---|---|---|---|
| Number of living cells ($\times 10^8$/ml) | 0.25 | 0.55 | 2.0 | 3.9 | 4.0 | 4.0 |
| $\Delta I$ ($\mu A/cm^2$) | 0.03 | 0.07 | 0.22 | 0.45 | 0.46 | 0.46 |

The foregoing results illustrate that there is a good correlation between the current values and the number of cells. Thus, the number of cells in the culture liquor can be simply, rapidly and continuously measured by measuring a difference in the current values.

EXAMPLE 2

In this example, Lactobacillus fermentum, ATCC 9338, is inoculated into 1 L of a medium containing 10 g of glucose, 10 g of peptone, 5 g of yeast extract, 0.25 g of $K_2HPO_4$, 0.1 g of $MgSO_4.7H_2O$, 0.005 g of $Fe_2SO_4.7H_2O$, 0.005 g of $MnSO_4.4H_2O$ and 0.005 g of NaCl, placed in the same jar fermenter as in Example 1, and subjected to stationary cultivation at 37° C. The relationship between the differences in voltage values ($\Delta V$) between the two electrodes as in Example 1 in the jar fermenter and the number of cells likewise determined separately by colony count are shown in Table 2.

TABLE 2

| Time (hr) | 1 | 3 | 5 | 7 | 9 |
|---|---|---|---|---|---|
| Number of living cells ($\times 10^8$/ml) | 2.0 | 7.1 | 21 | 33 | 34 |
| $\Delta V$ ($\mu V/cm^2$) | 0.16 | 0.55 | 1.8 | 2.7 | 2.7 |

The foregoing results illustrate that there is a good correlation between the voltage values and the number of cells.

EXAMPLE 3

In this example, Bacillus subtilis, ATCC 6633, is inoculated in 1 L of a medium containing 10 g of glucose, 10 g of peptone, 5 g of meat extract and 5 g of NaCl, placed in the same jar fermenter as in Example 1, and subjected to aerobic cultivation at 37° C. The same electrode systems as in Example 1 are placed in the jar fermenter; and the same measurements as in Example 1 are repeated. The results are given in Table 3.

TABLE 3

| Time (hr) | 2 | 4 | 6 | 8 | 12 |
|---|---|---|---|---|---|
| Number of living cells ($\times 10^8$/ml) | 1.5 | 5.1 | 10 | 16 | 18 |
| $\Delta I$ ($\mu A/cm^2$) | 0.03 | 0.07 | 0.13 | 0.25 | 0.27 |

As is evident from the foregoing table, there is a good correlation between differences in the current values between the two electrode systems and the number of cells.

EXAMPLE 4

In this example, the bread yeast (Saccharomyces cerevisiae) used in Example 1 under the same conditions as in Example 1 is subjected to aerobic cultivation. Two units of electrolytic electrode systems, as shown in FIG. 2, are placed in the cultivation tank. For both cathode and anode, platinum plates (1×1 cm) are used and a potential difference therebetween is set to 300 mV. One of the cathodes is covered with a cellulose membrane for dialysis. The differences ($\Delta I$) in current values between the two units of the electrolytic electrode systems as compared to the number of cells (number of living cells) determined at various times separately by colony count method are given in Table 4.

TABLE 4

| Time (hr) | 3 | 5 | 7 | 9 | 12 |
|---|---|---|---|---|---|
| Number of living cells ($\times 10^8$/ml) | 0.23 | 0.51 | 1.2 | 2.9 | 4.1 |
| $\Delta I$ ($\mu A/cm^2$) | 0.05 | 0.10 | 0.20 | 0.50 | 0.71 |

As is evident from the foregoing table, there is a good correlation between differences in the current value and the number of cells.

EXAMPLE 5

Micromonospora olivoasterospora [ATCC 31100] is inoculated in 1 L of a midium containing 30 g of soluble starch, 30 g of dried yeast, 3 g of $K_2HPO_4$, 1 g of $KH_2PO_4$, 0.5 g of $MgSO_4.7H_2O$, 0.2 g of NaCl, 0.1 g of $CaCO_3$ (pH 7.2 before sterilization) and cultivated by the same jar-fermentation as in Example 1 under aerobic condition at 30° C.

In the course of the fermentation, an aliquot of the broth is sampled out with time.

When the same electrodes (1) as in Example 1 is inserted in these samples withdrawn, currents obtained from the electrode increase with the fermentation time. Table 5 shows the correlation between currents and dry cell weights of these samples.

TABLE 5

| Time (hr) | 6 | 11 | 21 | 24 | 26 |
|---|---|---|---|---|---|
| Dry cell weight (mg/ml) | 13.6 | 18.6 | 34.5 | 39.8 | 42.5 |
| Current ($\mu A$) | 0.16 | 0.26 | 0.43 | 0.61 | 0.63 |

The results show a good correlation between the current and the dry cell weight.

In Actinomycetes, therefore, it is clear that the cell weight (the cell growth or the activity of the cell) can be simply and rapidly determined by using the same electrode system as in Example 1.

What is claimed is:

1. A method for determining the unknown number of living cells or total number of active parts in a liquid medium by measuring the difference between the current value or potential value of said microorganism and the current value or potential value of said liquid medium and correlating said measured difference with a current or potential difference which corresponds to a known amount of said microorganism.

2. A method according to claim 1 wherein said measurement is carried out by suspending in said liquid medium two electrode systems, each having a cathode, an internal electrolyte and a liquid junction and each having an exposed anode, one of said anodes being covered with a microorganism-impermeable membrane; and comparing the current value or potential value of said two electrode systems.

3. A method according to claim 1 wherein said measurement is carried out by suspending in said liquid medium two electrolytic electrode potentiostatic systems comprising two exposed electrodes and a reference calomel electrode, one of said electrolytic electrode systems having one of said exposed electrode (anode) being covered with a microorganism-impermeable membrane, and by comparing the current value or potential value of said two electrolytic electrode systems.

4. Apparatus for measuring microorganism activity in a liquid medium which comprises two electrode systems each of which comprises a cathode with an inside electrolyte having a liquid junction with said liquid medium and an exposed anode, wherein the exposed anode of one of said systems is covered with a microorganism-impermeable membrane for measuring activity of the microorganism on the outer side of said membrane; each of said cathodes and anodes being arranged in parallel and being connected to an ammeter or potentiometer.

* * * * *